ional Apgeek United States Patent [19]

Schaaf

[11] 4,097,601

[45] Jun. 27, 1978

[54] BONE DEPOSITION BY 2-DESCARBOXY-2-(TETRAZOL-5-YL)-11-DEXOSY-16-ARYL PROSTAGLANDINS

[75] Inventor: Thomas Ken Schaaf, Old Lyme, Conn.

[73] Assignee: Pfizer Inc., New York, N.Y.

[21] Appl. No.: 827,935

[22] Filed: Aug. 26, 1977

[51] Int. Cl.$^2$ .......................................... A61K 31/41
[52] U.S. Cl. ................................................ 424/269
[58] Field of Search ......................................... 424/269

[56] References Cited

U.S. PATENT DOCUMENTS 3,932,389   1/1976   Johnson et al. ....................... 424/269

*Primary Examiner*—Sam Rosen
*Attorney, Agent, or Firm*—Connolly and Hutz

[57] ABSTRACT

Bone deposition in animals is produced by administration of 2-descarboxy-2-(tetrazol-5-yl)-11-desoxy-16-aryl-ω-tetranor prostaglandins of the E series, their C-15 keto isomers, and the pharmaceutically acceptable salts thereof.

7 Claims, No Drawings

BONE DEPOSITION BY 2-DESCARBOXY-2-(TETRAZOL-5-YL)-11-DEXOSY-16-ARYL PROSTAGLANDINS

BACKGROUND OF THE INVENTION

The invention relates to the discovery that 2-descarboxy-2-(tetrazol-5-yl)-11-desoxy-16-aryl-ω-tetranor prostaglandins of the E series are able to stimulate bone reformation. Their synthesis and structure are disclosed in U.S. Pat. No. 3,932,389.

Bone, characteristically, is the main organ of the body that stands against the stress and strain of movement and work done by the body. This function requires both strength and rigidity of the bone and necessitates constant rebuilding of bone tissue. The result is a dynamic balance of formation, resorption and maintenance of the materials composing the tissue so that the bone strength is projected along the stress vector caused by external force on the bone.

The bone as living tissue is composed of cells, osteoid which is the extracellular organic matrix and osteominerals which are complex inorganic salts. The cells do all the work of formation, resorption and maintenance in the bone while the osteoid and the osteominerals provide the resiliency and strength characteristic of the bone. Morphologically the cells are divided into osteoblasts, osteoclasts and osteocytes which perform the functions of formation, resorption and maintenance of bone respectively. Collagen and ground substance form the two parts of the organic matrix called the osteoid. The former consists of cross-linked protein while the latter consists of glycol proteins functioning as cementing material. The osteominerals exist in both the amorphous and crystalline states and form a bed around the osteoid. Of the many complex minerals present, the most important and plentiful is calcium phosphate.

The osteoblasts and osteocytes control the metabolism of collagen, glycol proteins and minerals while the osteoclasts, which are multinuclear in nature cause resorption of collagen by enzymatic lysing action. The laying down of bone by the osteoblasts is regulated indirectly by two hormones, parathyroid hormone and thyrocalcitonin. Their secretion is a response to changes in the serum calcium level and their effect is to normalize the serum calcium level. The result is the use of bone by the body as a reservoir for removal or deposition of calcium in response to this hormone stimulation. The most important growth factor, however, is external stress without which there can be no stimulation of bone growth.

When the dynamic balance between bone resorption and bone formation is upset, the usual result is loss of bone density. The osteoblasts and osteocytes fail to maintain the regular growth of bone while the osteoclasts continue to lyse and dissolve bone. The result is a loss of collagen and osteominerals thus providing a thin shell of brittle bone in a poor condition to withstand stress.

There are many causes of the disruption of the dynamic balance resulting in loss of bone density. They are: osteopenia which includes such diseases as post menopausal osteoporosis and senile osteoporosis, osteomalacea, cystica fibrosa, osteogenic carcinomas and tumors, osteolysis and peridontal disease. Bone fracture also disrupts the normal dynamic balance between bone growth and resorption but it doesn't result in a loss of bone density. The usual treatment for bone wasting includes exercise and a diet rich in protein and calcium. However, it usually doesn't cure but simply arrests the ultimate debilitation. Obviously, osteogenic carcinomas and tumors have additional requirements for their treatment. In addition to exercise and diet, traditional treatment of bone wasting disorders has also relied upon the efficacy of such drugs as estrogens and anabolic hormones.

While some types of prostaglandins are reported to cause an increase in bone deposition, that affect is not a general phenomenon. U.S. Pat. Nos. 4,000,309, 3,982,016 and 4,018,892 all describe the bone deposition effects resulting from the administration of 16-aryl-13,14-dihydro-PGE$_2$ p-biphenyl esters to animals. However, the usual effect exhibited when prostaglandins are administered is not stimulation of bone deposition but bone resorption. The natural prostaglandins, PGE, PGF, PGA and PGB, of the one and two series all are reported to stimulate bone resorption in vitro (J. W. Dietrick, et al *Prostaglandins*, 10,231 (1975)). It is, thus, highly unlikely that any particular synthetic prostaglandin will exhibit bone deposition activity.

In view of the bone resorption characteristics of natural prostaglandins and the independent structures of the prostaglandins used in the present invention compared to those used in the U.S. patents supra describing a method of deposition, it has been suprisingly found that 2-descarboxy-2(tetrazol-5-yl)-11-desoxy-16-aryl-ω-tetranor prostaglandins may be used to cause increased bone deposition in animals.

SUMMARY OF THE INVENTION

In accordance with the present invention, a method for the treatment of bone disorders has been discovered which utilizes the administration of a prostaglandin to increase the amount of both the osteomineral deposit and the osteoid present within the bone. The prostaglandins producing this effect have the structure

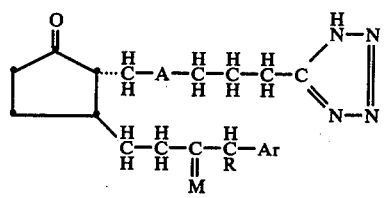

and the pharmacologically acceptable salts wherein:
A is ethylene or cis-vinylene;
M is oxo,

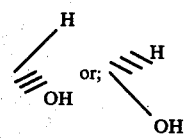

R is hydrogen or methyl; and
Ar is phenyl or monosubstituted phenyl, said monosubstituent being fluoro, chloro, bromo, trifluoromethyl, methyl, methoxy and phenyl.

The preferred prostaglandins to be used in the treatment of bone wasting disorders are 2-descarboxy-2-(tetrazol-5-yl)-11-desoxy-13,14-dihydro-16-phenyl-ω-tetranor-prostaglandin E$_2$, 2-descarboxy-2-(tetrazol-5-yl)-11-desoxy-16-phenyl-ω-tetranor-prostaglandin E$_0$, the corresponding C-15 epimers, the corresponding C-15 keto isomers and the magnesium salts of the preferred compounds.

Especially preferred are the magnesium salts of 2-descarboxy-2-(tetrazol-5-yl)-11-desoxy-16-phenyl-ω-tetranor prostaglandin $E_0$ and 2-descarboxy-2-(tetrazol-5-yl)-11-desoxy-15-keto-16-phenyl-ω-tetranorprostaglandin $E_0$.

The method is especially useful when the bone disorder to be treated is osteopenia, including osteoporosis, osteomalacia, osteitis, fibrosa cystica, osteolysis, a pathological change in the dynamic balance of the blood serum calcium and bone calcium levels, peridontal disease, bone fracture and bone loss associated with primary bone tumors.

The preferred routes of administration include oral tablets or capsules and injection. For oral administration the prostaglandin may be given in a suspension or solution with water, ethyl alcohol or vegetable oil or administered orally in a tablet or capsule form alone or in combination with excipients and solid diluents such as corn starch, talc, gum arabic, acacia, polyvinylpyrrolidone, clay, sucrose or dextrose at doses containing 2 microgram /kg. to 0.2 mg./kg. of the prostaglandin with up to 5 doses per day. For injection, the prostaglandin may be given intravenously, intramuscularly or subcutaneously in a sterile mixture or solution with such diluents as normal saline or water and ethyl alcohol at doses containing 0.5 micrograms/kg. to 50 micrograms/kg. of the prostaglandin with up to 5 doses per day.

DETAILED DESCRIPTION OF THE INVENTION

The structure and prostaglandins used in this invention as well as method for their synthesis have been disclosed and the compounds claimed in U.S. Pat. No. 3,932,389. Briefly, they are synthesized using the well-known Corey prostaglandin synthesis route and employing 2-[5α-hydroxy-2β-formyl-cyclopent-1α-yl]acetic acid γ-lactone, dimethyl 2-oxo-3-arylpropyl or butyl phosphonate wherein the aryl group is defined as above and [4-(tetrazol-5-yl)-n-butyl]triphenylphosphonium bromide as starting materials for the cyclopentyl nucleus and the bottom and top side chains.

In addition to the isolated prostaglandins themselves, physical compositions of the prostaglandins used for this invention consist of a variety of pharmacologically acceptable salts. These useful salts are formed by the combination of the prostaglandins described supra and pharmacologically acceptable metal hydroxides, methoxides and ethoxides, ammonium hydroxide, amines and quaternary ammonium halide salts. Methods to form these salts are well-known in the art. Especially preferred metal cations to be used in the combinations are those derived from alkali metals such as lithium, sodium and potassium and from alkaline earth metals such as magnesium and calcium, although cationic forms of other metals such as aluminum, zinc and iron are within the scope of this invention. Pharmacologically acceptable amine cations to be used in the combination are those derived from primary, secondary and tertiary amines. Examples of suitable amines are methyl amine, dimethyl amine, triethyl amine, ethyl amine, benzyl amine, alpha phenylethyl amine, beta phenylethyl amine as well as heterocyclic amines such as piperidine, morpholine, pyrrolidine and piperazine. Other amines include those containing water solubilizing or hydrophilic groups such as mono, di and tri ethanol amine, galactamine, n-methyl glucosamine, ephedrine, phenylephedrine, epinephrine, procaine and the like. Examples of suitable pharmacologically acceptable quaternary ammonium cations to be used in the combination are tetramethylammonium, tetraethylammonium, benzyltrimethylammonium phenyltriethylammonium and the like. Examples of excipients and binders which can be used to form tablets or capsules with the prostaglandins or their salts used in this invention include polyvinylpyrrolidone, sodium citrate, calcium carbonate, dicalcium phosphates, starch, alginic acid, complex silicates, milk sugar (lactose) gelatin, acacia, gum arabic corn starch, talc, sucrose, dextrose and the like. A typical formulation is composed of the desired amount of prostaglandin or its salt and from 5 to 20% corn starch and from 75 to 95% lactose compressed into tablet form.

The prostaglandins used for this invention can be administered in a variety of pharmaceutical preparations as described above. Although the particular dose formulation and route of administration are dependent upon each patient's unique condition and the wisdom of his attending physician, the guidelines set forth infra for the 2-descarboxy-(tetrazol-5-yl)-11-desoxy-16-aryl-ω-tetranor-prostaglandins and their pharmacologically acceptable salts describe the method of treatment of bone wasting disorders according to the present invention. For deposition of the bone tissue, the prostaglandins or their salts used in this invention may be administered orally in tablet or capsule form in formulations as described supra at doses containing 2 microgram/kg. to 0.2 mg/kg. of the prostaglandin with up to 5 doses per day. The prostaglandins may also be administered by injection intramuscularly, intravenously or subcutaneously in a sterile mixture or solution with diluents such as normal saline or water and ethyl alcohol at doses containing 0.5 microgram/kg. to 50 micrograms/kg. of the prostaglandin with up to 5 doses per day.

The following example describes the efficacy of the prostaglandins used in this invention in causing bone deposition in various species of animals. It is meant to be illustrative only and in no way limits the scope of the claims.

Twelve male and 12 female cynomolgus monkeys were assigned to four groups of three males and three females each. Three of these groups were given the test compound, the magnesium salt of 2-descarboxy-2-(tetrazol-5-yl)-11-desoxy-15-keto-16-phenyl-ω-tetranor $PGE_o$, in gelatin capsules at dose levels of 0.5, 0.25 and 0.1 mg./kg. once daily for 98 days. The test compound was administered as a 1% cornstarch-lactose blend containing 10% cornstarch, 89% lactose and 1% test compound. The three dose groups therefore were given 50, 25 and 10 mg. of this blend /kg./day respectively. The fourth group serving as controls received empty gelatin capsules only. Five of six high dose level animals exhibited bilateral, diaphyseal thickening of the long bones (humerus, radius, ulna, femur, tibia, fibula). Histologically, this lesion is characterized by periosteal new bone formation; and, concomitant lysis of cortical and periosteal new bone. Withdrawal of the drug for a short period of time did not cause complete reversion of the bone to its original state. Other clinical chemistry appeared to be within the normal range for the cynomolgus monkey.

What is claimed is:

1. In the treatment of bone disorders, a method to increase the amount of both the osteomineral deposit and the osteoid present within bone by administration to a subject in need of said treatment an effective amount of a prostaglandin having the structure

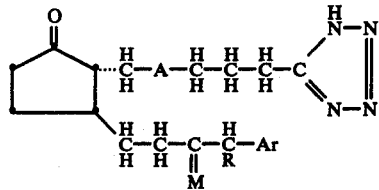

or the pharmacologically acceptable salts thereof wherein:

A is ethylene or cis-vinylene:
M is oxo,

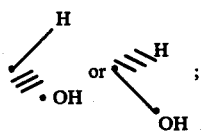

R is hydrogen or methyl;
and Ar is phenyl or monosubstituted phenyl, said monosubstituent being fluoro, chloro, bromo, trifluoromethyl, methyl, methoxy and phenyl.

2. A method according to claim 1 wherein M of said prostaglandin is oxo, R is hydrogen and Ar is phenyl.

3. A method according to claim 1 wherein M of said prostaglandin is

R is hydrogen and Ar is phenyl.

4. A method according to claim 2 wherein the magnesium salt of 2-descarboxy-2-(tetrazol-5-yl)-11-desoxy-15-keto-16-phenyl-ω-tetranor prostaglandin $E_0$ is administered.

5. A method according to claim 1 wherein said bone disorder is osteopenia including osteoporosis, osteomalacia, osteitis fibrosa cystica and osteolysis; a pathological change in the dynamic balance of the blood serum calcium and bone calcium levels; peridontal disease; a fracture and said treatment enhances the healing rate of said fracture or bone loss associated with osteogenic carcinomas and tumors.

6. A method according to claim 1 wherein said prostaglandin is administered orally in a suspension or solution with water, ethyl alcohol or vegetable oil or administered orally in tablet or capsule form alone or in combination with excipients, binders and solid diluents such as corn starch, talc, gum arabic acacia, polyvinylpyrrolidone, clay, lactose, sucrose or dextrose at doses containing 2 microgram/kg to 0.2 milligrams/kg of said prostaglandin with up to 5 doses per day.

7. A method according to claim 1 wherein said prostaglandin is administered by injection intramuscularly, intravenously or subcutaneoulsy in a sterile mixture or solution with such diluents as normal saline or water and ethyl alcohol at doses containing 0.5 microgram/kg to 50 micrograms/kg of said prostaglandin with up to 5 doses per day.

* * * * *